(12) United States Patent
Hennigan

(10) Patent No.: US 10,017,450 B2
(45) Date of Patent: Jul. 10, 2018

(54) METHOD OF OPERATING A HEAVY ENDS COLUMN IN AN ACETIC ACID PRODUCTION PROCESS

(71) Applicants: BP CHEMICALS LIMITED, Sunbury-on-Thames, Middlesex (GB); Sean Anthony Hennigan, Hull, East Yorkshire (GB)

(72) Inventor: Sean Anthony Hennigan, East Yorkshire (GB)

(73) Assignee: BP CHEMICALS LIMITED, Sunbury-on-Thames (GB)

( * ) Notice: Subject to any disclaimer, the term of this patent is extended or adjusted under 35 U.S.C. 154(b) by 0 days.

(21) Appl. No.: 15/315,260

(22) PCT Filed: Aug. 4, 2015

(86) PCT No.: PCT/EP2015/068001
§ 371 (c)(1),
(2) Date: Nov. 30, 2016

(87) PCT Pub. No.: WO2016/020410
PCT Pub. Date: Feb. 11, 2016

(65) Prior Publication Data
US 2017/0190649 A1    Jul. 6, 2017

(30) Foreign Application Priority Data

Aug. 5, 2014  (EP) .................................. 14179893

(51) Int. Cl.
*C07C 51/44*    (2006.01)
*C07C 51/12*    (2006.01)

(52) U.S. Cl.
CPC .............. *C07C 51/44* (2013.01); *C07C 51/12* (2013.01)

(58) Field of Classification Search
CPC .............................. C07C 51/44; C07C 51/12
See application file for complete search history.

(56) References Cited

U.S. PATENT DOCUMENTS 5,194,122 A * 3/1993 Bleeker ..................... C05F 3/00
                                                        203/34
2010/0063319 A1   3/2010 Brtko et al.

FOREIGN PATENT DOCUMENTS

| EP | 0 849 250 A1 | 6/1998 |
| EP | 0849250 A1 * | 6/1998 |
| WO | WO 209/042078 A1 | 4/2009 |
| WO | WO 2012/014393 A1 | 2/2012 |

OTHER PUBLICATIONS

Howard, M.J., et al; "$C_1$ to acetyls: catalysis and process"; *Catalysis Today*, 18, pp. 325-354 (1993).

* cited by examiner

*Primary Examiner* — Paul A Zucker
(74) *Attorney, Agent, or Firm* — Nixon & Vanderhye P.C.

(57) ABSTRACT

Method of operating a heavy ends column in an acetic acid production unit having a reaction section, a light ends recovery section including a light ends distillation column, and a heavy ends column. A stream containing acetic acid and propionic acid obtained from the light ends recovery section is fed to the heavy ends column through a feed inlet positioned at an intermediate point in the heavy ends column. A product stream containing acetic acid is withdrawn from the heavy ends column through a sidedraw product outlet position above the feed inlet, and a product stream containing the propionic acid is withdrawn from the heavy ends column through a heavy product outlet positioned below the feed inlet. The pressure in the heavy ends column above the feed inlet is lower than the pressure of the stream containing acetic acid and propionic acid that is fed to the heavy ends column.

29 Claims, 1 Drawing Sheet

METHOD OF OPERATING A HEAVY ENDS COLUMN IN AN ACETIC ACID PRODUCTION PROCESS

This application is the U.S. national phase of International Application No. PCT/EP2015/068001 filed Aug. 4, 2015 which designated the U.S. and claims priority to European Patent Application No. 14179893.4 filed Aug. 5, 2014, the entire contents of each of which are hereby incorporated by reference.

The present invention relates to a method of operating a heavy ends column in an acetic acid production unit. The present invention further relates to a process for the separation of acetic acid from a stream comprising acetic acid and propionic acid in a distillation column.

BACKGROUND OF THE INVENTION

Acetic acid is a well-known commodity chemical which has many industrial uses.

Various methods for producing acetic acid industrially are well known, many such processes produce propionic acid, either as a by-product or a co-product. In order for the acetic acid to meet necessary specifications for use and/or sale, it is often necessary to subject the acetic acid product to a process for the removal of propionic acid.

EP 0 849 250 A1 discloses a process for the production of an acetic acid process stream comprising less than 400 ppm propionic acid and less than 1500 ppm water, which process comprises the steps:—
(a) feeding methanol and/or a reactive derivative thereof and carbon monoxide to a carbonylation reactor in which there is maintained during the course of the process a liquid reaction composition comprising an iridium carbonylation catalyst, methyl iodide cocatalyst, optionally one or more promoters selected from the group consisting of ruthenium, osmium, rhenium, cadmium, mercury, zinc, gallium, indium and tungsten, a finite amount of water at a concentration of less than about 8% by weight, methyl acetate, acetic acid, and propionic acid by-product and its precursors;
(b) withdrawing liquid reaction composition from the carbonylation reactor and introducing at least part of the withdrawn liquid reaction composition, with or without the addition of heat, to a flash zone to form a vapour fraction comprising water, acetic acid product, propionic acid by-product, methyl acetate, methyl iodide and propionic acid precursors, and a liquid fraction comprising involatile iridium catalyst, involatile optional promoter or promoters, acetic acid and water;
(c) recycling the liquid fraction from the flash zone to the carbonylation reactor;
(d) introducing the vapour fraction from the flash zone into a first distillation zone;
(e) removing from the first distillation zone at a point above the introduction point of the flash zone vapour fraction a light ends recycle stream comprising water, methyl acetate, methyl iodide, acetic acid and propionic acid precursors which stream is recycled in whole or in part to the carbonylation reactor, and
(f) removing from the first distillation zone at a point below the introduction point of the flash zone vapour fraction, a process stream comprising acetic acid product, propionic acid by-product, and less than 1500 ppm water and,
(g) if the process stream removed in step (f) comprises greater than 400 ppm propionic acid introducing said stream into a second distillation column, removing from a point below the introduction point of the stream from (f) propionic acid by-product and from a point above the introduction point of the stream from (f) an acetic acid process stream containing less than 400 ppm propionic acid and less than 1500 ppm water.

Only limited details of the configuration and operation of the optional second distillation column in step (g) of EP 0 849 250 A1 are provided.

WO 2009/042078 A1 discloses a method and apparatus for making acetic acid with improved purification. The improvements in the purification provided in WO 2009/042078 A1 are not directly related to the configuration and operation of the heavy ends column disclosed therein, and only limited details of the configuration and operation of the heavy ends column are provided.

WO 2012/014393 A1 provides a process for producing acetic acid with a high purity. Disclosed in WO 2012/014393 A1 is a second distillation column which separates at least part of a higher boiling component (e.g., propionic acid) from the bottom of the column. Only limited details of the configuration and operation of the second distillation column of WO 2012/014393 A1 are provided.

US 2010/0063319 A1 provides a process for producing acetic acid, the process comprising the carbonylation of methanol to form a reaction mixture comprising a catalyst, catalyst stabiliser, acetic acid, methanol, methyl iodide, methyl acetate, water and carbon monoxide, and introducing at least a portion of the reaction mixture to a distillation column to separate into a bottom stream comprising the catalyst and catalyst stabiliser, a sidedraw stream comprising acetic acid and water, and an overhead stream comprising methanol, methyl acetate, methyl iodide and water. The process provided by US 2010/0063319 A1 eliminates the use of a flash tank. The sidedraw stream removed from the distillation column is optionally subjected to further purification such as drying-distillation to remove water and heavy-ends distillation to remove heavy impurities such as propionic acid. US 2010/0063319 A1 does not provide any details regarding the configuration or the operation of the optional heavy-ends distillation.

The operation of a heavy ends column for the removal of propionic acid from an acetic acid product requires large amounts of energy due to the fact that the by-product propionic acid has a higher boiling point than the acetic acid.

SUMMARY OF THE INVENTION

There remains a need in the art for improvements in the operation of the heavy ends column of an acetic acid production unit, such as improvements in the energy usage in the operation of the heavy ends distillation column.

The present invention provides a method of operating a heavy ends column in an acetic acid production unit, said production unit comprising at least a reaction section, a light ends recovery section comprising a light ends distillation column, and a heavy ends column, wherein a stream comprising acetic acid and propionic acid obtained from the light ends recovery section is fed to the heavy ends column through a feed inlet positioned at an intermediate point in the heavy ends column, a product stream comprising essentially acetic acid is withdrawn from the heavy ends column through a sidedraw product outlet position above the feed inlet, and a product stream comprising the propionic acid is withdrawn from the heavy ends column through a heavy product outlet positioned below the feed inlet, wherein the heavy ends column is operated under conditions such that the pressure in the heavy ends column above the feed inlet is lower than the pressure of the stream comprising acetic acid and propionic acid that is fed to the heavy ends column, and wherein the head pressure of the heavy ends column is below 1.0 bara, the number of theoretical separation stages between the feed inlet and the sidedraw product outlet is at least 5, preferably at least 7, more preferably at least 10, and the pressure drop in the part of the heavy ends column between the feed inlet and the sidedraw product outlet is at most 10 mbar per theoretical separation stage.

The present invention further provides a process for the separation of acetic acid from a stream comprising acetic acid and propionic acid, wherein in said process the stream comprising acetic acid and propionic acid is fed to a distillation column through a feed inlet positioned at an intermediate point in the distillation column, a product stream comprising essentially acetic acid is withdrawn from the distillation column through a sidedraw product outlet position above the feed inlet, and a product stream comprising the propionic acid is withdrawn from the distillation column through a heavy product outlet positioned below the feed inlet, wherein the distillation column is operated under conditions such that the pressure in the distillation column above the feed inlet is lower than the pressure of the stream comprising acetic acid and propionic acid that is fed to the distillation column, and wherein the distillation column configured such that the head pressure is below 1.0 bara, the number of theoretical separation stages between the feed inlet and the sidedraw product outlet is at least 5, preferably at least 7, more preferably at least 10, and the pressure drop in the part of the distillation column between the feed inlet and the sidedraw product outlet is at most 10 mbar per theoretical separation stage.

The present invention yet further provides a process for the production of acetic acid in an acetic acid production unit comprising a reaction section, a light ends recovery section comprising a light ends column, and a heavy ends column, wherein said process comprises the steps:

(a) in the reaction section, carbonylating methanol and/or a reactive derivative thereof with carbon monoxide in a liquid reaction composition comprising a Group VIII metal carbonylation catalyst, a methyl iodide cocatalyst, acetic acid, water, methyl acetate, propionic by-product, and optionally a promoter;

(b) withdrawing at least a portion of the liquid reaction composition from the reaction section and introducing the withdrawn liquid reaction composition into a flash zone to produce a vapour fraction comprising water, acetic acid, methyl acetate, methyl iodide, and propionic acid by-product, and a liquid fraction comprising the catalyst;

(c) recycling the liquid fraction from the flash zone to the reaction section;

(d) feeding the vapour fraction obtained from the flash zone to the light ends column of the light ends recovery section;

(e) removing a stream comprising acetic acid and propionic acid from the light ends column;

(f) optionally drying the stream comprising acetic acid and propionic acid removed from the light ends column in a separate drying column; and (g) feeding the stream comprising acetic acid and propionic acid to the heavy ends column through a feed inlet positioned at an intermediate point in the heavy ends column, withdrawing a product stream comprising essentially acetic acid through a sidedraw product outlet position above the feed inlet, and withdrawing a product stream comprising the propionic acid through a heavy product outlet positioned below the feed inlet, wherein the heavy ends column is operated under conditions such that the pressure in the heavy ends column above the feed inlet is lower than the pressure of the stream comprising acetic acid and propionic acid that is fed to the heavy ends column, and wherein the head pressure of the heavy ends column is below 1.0 bara, the number of theoretical separation stages between the feed inlet and the sidedraw product outlet is at least 5, preferably at least 7, more preferably at least 10, and the pressure drop in the part of the heavy ends column between the feed inlet and the sidedraw product outlet is at most 10 mbar per theoretical separation stage.

The present invention provides a method of operating a heavy ends column in an acetic acid production unit which has reduced energy requirements for the reboiler compared to heavy ends column configurations typically used. The present invention also independently provides a process for the separation of a stream comprising essentially acetic acid from a stream comprising acetic acid and propionic acid using a heavy ends column as herein defined as a distillation column.

It has been found that the reboiler energy requirements for a heavy end column in an acetic acid production unit can be reduced by using column mass transfer devices (structures within the distillation column used to improve fractionation, such as trays and packing) having a low pressure drop per theoretical stage of separation, and that surprisingly the use of column internals having a low pressure drop per theoretical stage of separation in the part of the column between the feed inlet and the sidedraw product outlet provides a much more significant reduction in the reboiler energy requirements than the use of such column mass transfer devices in other parts of the heavy ends distillation column.

Thus, it has been surprisingly found that by operating a heavy ends column with a low pressure drop per theoretical separation stage in the part of the heavy ends column between the feed inlet and the sidedraw product outlet, in combination with a head pressure below 1.0 bara, a significantly lower reboiler duty (in terms of energy) may be used whilst still maintaining the same separation performance. It has also been surprisingly observed that for configurations which do not have a low pressure drop per theoretical separation stage in the part of the heavy ends column between the feed inlet and the sidedraw product outlet, the reboiler duty (in terms of energy) is not significantly reduced by the reduction in pressure drop per theoretical separation stage in the parts of the heavy ends column above the sidedraw product outlet and below the feed inlet, even when a greater total number of theoretical stages are present in the parts of the heavy ends column above the sidedraw product outlet and below the feed inlet compared to the part between the feed inlet and the sidedraw product outlet.

By the term "an acetic acid production unit" as used in the present invention, it is meant a unit that produces a purified acetic acid product.

In the present invention, the acetic acid production unit comprises a reaction section, a light ends recovery section comprising a light ends column, and a heavy ends column. Typically, a flash zone is employed between the reaction section and the light ends recovery section. Other reactors or distillation sections may also be present.

In the present invention, the process by which the acetic acid is produced is one which also produces propionic acid, either as a by-product or co-product, including processes which produce precursor compounds to propionic acid which are subsequently converted to propionic acid within the acetic acid production unit. In one particular embodiment of the present invention, the process by which the acetic acid is produced is by the carbonylation of methanol and/or a reactive derivative thereof with carbon monoxide in the presence of a Group VIII metal catalyst system. Production unit equipment for the manufacture of acetic acid by the carbonylation of methanol and/or a reactive derivative thereof with carbon monoxide in the presence of a Group VIII metal catalyst system, and the operation thereof is well known in the art.

The reaction section of the acetic acid production unit as referred to in the present invention may be any suitable reaction unit which may be used to produce an acetic acid containing product stream. In one particular embodiment, the reaction section of the acetic acid production unit is a reactor or more than one reactor within which acetic acid may be produced by the carbonylation of methanol and/or a reactive derivative thereof with carbon monoxide in the presence of a Group VIII metal catalyst system. Suitable reactors and configuration of multiple reactors which may be employed in the carbonylation of methanol and/or a reactive derivative thereof are known in the art.

Within the reaction section of the acetic acid production unit, a suitable reaction for the production of acetic acid is performed; in one particular embodiment, the carbonylation of methanol and/or a reactive derivative thereof with carbon monoxide in the presence of a Group VIII metal carbonylation catalyst and methyl iodide is performed to produce acetic acid. Processes and Group VIII metal catalysts for the carbonylation of methanol are well-known in the art.

Processes for carbonylation of methanol and/or a reactive derivative thereof with carbon monoxide in the presence of a Group VIII metal catalyst system may be conducted as a homogeneous process or as a heterogeneous process.

Suitably, in a heterogeneous carbonylation process the Group VIII metal carbonylation catalyst, such as rhodium and/or iridium is supported on an inert support, such as carbon and activated carbon. Optionally, the catalyst may also comprise at least one metal promoter. Suitable metal promoters include ruthenium, iron, nickel, lithium and cobalt. The methanol reactant may be fed to the process in the liquid and/or vapour phase. Methyl iodide and optional water are preferably fed to the process in the vapour phase.

Suitably, a homogeneous liquid phase carbonylation process employs a liquid reaction composition comprising a Group VIII metal carbonylation catalyst, methyl iodide, methyl acetate and water, the liquid reaction composition would also comprise a quantity of propionic acid by-product.

Suitably, the Group VIII metal carbonylation catalyst in the liquid reaction composition is an iridium and/or rhodium-containing compound which is soluble in the liquid reaction composition. The iridium and/or rhodium carbonylation catalyst may be added to the liquid reaction composition in any suitable form which dissolves in the liquid reaction composition or is convertible to a soluble form.

Examples of suitable iridium-containing compounds which may be used in the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-$, $[Ir(CO)_2Br_2]^-$, $[Ir(CO)_2I_2]^-$, $[Ir(CH_3)I_3(CO)_2]^-$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates.

Suitably, the concentration of iridium catalyst in the liquid reaction composition is in the range 100 to 6000 ppm by weight of iridium.

Examples of suitable rhodium-containing compounds which may be used in the liquid reaction composition include $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3(PPh_3)_3$ and $RhCl(CO)(PPh_3)_2$.

Suitably, the concentration of rhodium catalyst in the liquid reaction composition is in the range from 1 ppm up to its limit of solubility in the reactor and/or product recovery system, typically in the range 10 to 1500 ppm by weight of rhodium.

Where the Group VIII metal carbonylation catalyst is an iridium carbonylation catalyst, the liquid reaction composition may optionally contain a promoter selected from the group consisting of ruthenium, osmium and rhenium.

Where the Group VIII metal carbonylation catalyst is a rhodium carbonylation catalyst, the liquid reaction composition may optionally contain a promoter selected from alkali metals and/or an organic iodide, such as a quaternary ammonium iodide. Preferably the promoter is lithium iodide.

The concentration of methyl acetate in the liquid reaction composition for rhodium-catalysed carbonylation is suitably in the range 0.1 to 70% by weight and for iridium-catalysed carbonylation is suitably in the range 1 to 70% by weight.

Water is present in the liquid reaction composition. Water is formed in situ in the liquid reaction composition by the esterification reaction between methanol and acetic acid product. Additional water may be introduced to the carbonylation reactor together with or separately from other components of the liquid reaction composition. Preferably, the concentration of water in the liquid reaction composition is in the range 0.1 to 15% by weight, more preferably 1 to 15% by weight.

By-product propionic acid is also present in the liquid reaction composition. Whilst the concentration of propionic acid in the liquid reaction composition will be dependent upon the exact catalyst system and conditions employed, a typical concentration of propionic acid in the liquid reaction composition may be in the range of 200 to 2500 ppmw, more typically in the range of from 400 to 2000 ppmw, such as in the range of from 600 to 1400 ppmw.

The concentration of methyl iodide used in the liquid reaction composition is preferably in the range 1 to 20% by weight.

A solvent, preferably acetic acid, may be used in the liquid reaction composition.

The carbonylation process employs carbon monoxide. The carbon monoxide may be essentially pure or may contain impurities such as carbon dioxide, methane, nitrogen hydrogen and noble gases.

Suitably, the partial pressure of carbon monoxide is from about 1 to about 70 bar, for example from about 1 to about 35 bar.

Suitably, the carbonylation process is carried out at a total pressure from about 10 to about 100 barg.

Suitably, the carbonylation process is carried out at a temperature from about 100 to about 300° C.

The carbonylation process may be operated as either a batch or continuous, preferably as a continuous process.

A flash zone is preferably employed between the reaction section and the light ends recovery section of the acetic acid production unit. The purpose of the flash zone is to separate the liquid reaction composition from the reaction section into (i) a vapour fraction comprising water, acetic acid product, methyl acetate, methyl iodide and propionic acid which is then introduced into a light ends column, and (ii)

a liquid fraction comprising the catalyst. The liquid fraction can be recycled to the reaction section.

Suitable equipment and conditions for use in the flash zone will be well known to those skilled in the art.

The light ends recovery section of the acetic acid production unit serves the purpose of separating at least the components which are more volatile than acetic acid from the stream passed to the light ends recovery section from the reaction section (or the flash zone when a flash zone is positioned between the reaction section and the light ends recovery section).

In the embodiment wherein the process by which the acetic acid is produced is by the carbonylation of methanol and/or a reactive derivative thereof with carbon monoxide in the presence of a Group VIII metal catalyst system, the light ends recovery section of the acetic acid production unit serves the dual purpose of crude acetic acid purification (of the liquid reaction composition from the reaction section and/or the vapour fraction from the flash zone) and of methyl iodide and methyl acetate for recycling to the reaction section.

In the embodiment wherein the process by which the acetic acid is produced is by the carbonylation of methanol and/or a reactive derivative thereof with carbon monoxide in the presence of a Group VIII metal catalyst system, the 'light ends column' is a distillation column which separates crude acetic acid product comprising acetic acid and propionic acid from the light ends, methyl iodide and methyl acetate. Thus, the term light ends column as used herein will encompass such distillation columns which are referred to in the art as 'light ends distillation columns' and 'combined light ends and drying columns'. A combined light ends and drying column is a light ends column in which water is removed from the afore-mentioned crude acetic acid product so as to produce a dry acetic acid product comprising acetic acid and propionic acid.

By the term "dry", "dried" and the like as used in reference to streams comprising acetic acid and optionally also propionic acid, it is meant streams containing at most 1500 ppmw of water.

Typically, when the acetic acid has been produced by the carbonylation of methanol and/or a reactive derivative thereof, the feed stream to the light ends column is a vapour stream comprising acetic acid, water, carbon monoxide, methyl acetate, methyl iodide and propionic acid. More typically, the vapour stream will be the vapour fraction obtained from a flash zone.

In the light ends column, the higher boiling acetic acid and propionic acid is separated from the lower boiling components such as methyl iodide and methyl acetate.

The conditions and configuration under which the light ends column is operated are not critical to the present invention provided that the separation of the acetic acid and propionic acid from the methyl iodide and methyl acetate is achieved. Suitably, the light ends column may have up to 40 theoretical stages. The column may be operated at any suitable pressure, for example a heads pressure of from 1.0 to 3.0 barg, typically from 1.0 to 2.5 barg, and a base pressure of from 1.2 to 3.8 barg, typically from 1.2 to 3.5 barg. The operating temperature of the light ends column will depend upon a number of factors, including the composition of the feed, heads and base streams and the operating pressure. Typical base temperatures may be in the range 125° C. to 180° C. and typical heads temperatures may be in the range 105° C. to 140° C.

In general, at least two streams are removed from the light ends column, a stream comprising acetic acid and propionic acid, and, as an overhead from the column, a vapour fraction comprising methyl acetate, water, acetic acid and carbon monoxide, and, where the acetic acid is produced by the carbonylation of methanol and/or a reactive derivative thereof, also methyl iodide.

The stream comprising acetic acid and propionic acid may be removed from any suitable point of the light ends column, for example, from below the feed point, or as a liquid or vapour from the base of the column.

The stream comprising acetic acid and propionic acid removed from the light ends column may, if required, be dried, for example in a drying column. A separate drying column is generally not required if the light ends column is a combined light ends distillation and drying column.

The separated water can be recycled to the reactor and/or removed from the process.

The second part of the light ends recovery section consists of a condenser section comprising one or more condensers and/or coolers to condense the overhead vapour fraction from the light ends column to produce a liquid fraction. Any suitable method known to condense the overhead vapour fraction to the liquid phase can be employed but typically this is achieved by cooling, using, for example at least one heat exchanger. The heat exchanger(s) may be supplied with water as cooling medium.

Those components of the overhead vapour fraction from the light ends column which are not condensed, for example carbon monoxide, carbon dioxide, inert gases, reaction by-product gases are removed from the condenser section as an off-gas stream. When the acetic acid has been produced by the carbonylation of methanol and/or a reactive derivative thereof, this off-gas stream comprises methyl iodide, present as entrained methyl iodide and/or evaporated methyl iodide, and generally also comprises some methyl acetate and water.

The liquid fraction from the condenser section comprises mainly methyl acetate, water and acetic acid, and, when the acetic acid has been produced by the carbonylation of methanol and/or a reactive derivative thereof, methyl iodide, but it may also contain entrained or dissolved gaseous components such as carbon monoxide, carbon dioxide and inert gases.

From the condenser section, the liquid fraction may be passed to a decanter where it is separated into two layers, a lower (organic) layer comprising methyl acetate, and, when the acetic acid has been produced by the carbonylation of methanol and/or a reactive derivative thereof, methyl iodide, and an upper (aqueous) layer comprising water. At least part of, preferably all of, the upper (aqueous) layer from the decanter is typically returned to a point at or near the top of the light ends column as a reflux stream. At least part of, preferably all of, the lower (organic) layer from the decanter is typically recycled to the reaction section.

Off-gas may also be withdrawn from the decanter.

The off-gas withdrawn from the light ends column and optionally from the decanter will typically be sent to an off-gas scrubbing unit before disposal.

In the present invention, the stream comprising acetic acid and propionic acid obtained from the light ends recovery section which is fed to the heavy ends column is preferably a dry acetic acid product comprising acetic acid and propionic acid. Thus, if the stream comprising acetic acid and propionic acid obtained from the light ends recovery section comprises more than 1500 ppmw water, it is preferably dried in a separate drying column before being passed to the heavy ends column. Suitable columns and conditions for drying acetic acid streams, including those containing propionic acid, having more than 1500 ppmw water are well known in the art and any such suitable process may be used.

The stream comprising acetic acid and propionic acid, preferably a dry stream comprising acetic acid and propionic acid, obtained from the light ends recovery section is then fed to a heavy ends column thorough a feed inlet positioned at an intermediate point in the column and a product stream comprising essentially acetic acid is withdrawn from the heavy ends column through a side-draw product outlet. A product stream comprising the propionic acid is also withdrawn from the heavy ends column through a heavy product outlet. Additional streams comprising acetic acid may also be removed from the heavy ends column, such as acetic acid streams removed as an overhead from the heavy ends column.

The product stream comprising essentially acetic acid withdrawn from the heavy ends column in the present invention will typically comprise at most 400 ppmw propionic acid, preferably less than 400 ppmw of propionic acid, more preferably less than 300 ppmw of propionic acid, such as 250 ppmw or less propionic acid. Preferably, the product stream comprising essentially acetic acid withdrawn from the heavy ends column in the present invention will comprise at most 400 ppmw propionic acid, preferably less than 400 ppmw of propionic acid, more preferably less than 300 ppmw of propionic acid, such as 250 ppmw or less propionic acid, and at most 1500 ppmw, preferably less than 1500 ppmw water.

In one particular embodiment of the present invention, the product stream comprising essentially acetic acid withdrawn from the heavy ends column in the present invention will comprise less than 400 ppmw of propionic acid (more preferably less than 300 ppmw of propionic acid, such as 250 ppmw or less propionic acid), less than 1500 ppmw water, and wherein the combined total amount of both propionic acid and water is at most 1500 ppmw.

The heavy ends column of the present invention is a distillation column comprising a feed inlet positioned at an intermediate point in the column, a sidedraw product outlet positioned at a point on the column which is above the feed inlet, and a heavy product outlet positioned at a point of the column which is below the feed inlet. The heavy ends column of the present invention may be defined in three parts defined relative to the feed inlet and the sidedraw product outlet; namely, a top section which consists of the distillation column which is above the sidedraw product outlet, a middle section which is between the sidedraw product outlet and the feed inlet, and a bottom section which is below the feed inlet.

In the heavy ends column of the present invention, the number of theoretical separation stages in the middle section (the part which is between the feed inlet and the sidedraw product outlet) is at least 5, preferably at least 7, more preferably at least 10. In a particular embodiment of the present invention, the number of theoretical separation stages in the middle section in the range of from 10 to 20, preferably in the range of from 12 to 16.

The pressure drop in the middle section of the heavy ends column is at most 10 mbar per theoretical separation stage; that is, the overall pressure drop in the middle section of the heavy ends column shall not exceed the total pressure drop value calculated by the multiplication of the number of theoretical separation stages present in the middle section of the heavy ends column with 10 mbar, for example, if the middle section of the heavy ends column contains 15 theoretical separation stages, the maximum pressure drop in the middle section of the heavy ends column is 150 mbar. In a particular embodiment of the present invention, the pressure drop across the middle section of the heavy ends column (i.e. total pressure drop between the feed inlet and the sidedraw product outlet) is at most 80 mbar, preferably at most 60 mbar.

The number of theoretical separation stages in the top section and the bottom section of the heavy ends column is not critical to the present invention and may readily be determined by a person skilled in the art.

The heavy ends column will also comprise other conventional features of a distillation column, such as having an outlet at the top of the column which is connected to a condenser and at, or connected to, the base of the heavy ends column is a reboiler. Additional inlets and/or outlets may also be present on the heavy ends column, such as an a reflux inlet positioned at or near the top of the column to return any liquids condensed in the condenser, additional product outlets may also be present on the heavy ends column, and, in configurations wherein the reboiler does not form part of the distillation column, an inlet at or near the base of the column. The configuration and operation of such additional components of the heavy ends column is well known in the art.

The product stream comprising essentially acetic acid is withdrawn from the heavy ends column through a sidedraw outlet. The configuration of a suitable sidedraw product outlet is well known in the art and any such suitable sidedraw outlet configuration may be used.

In one specific configuration of a sidedraw product outlet, the sidedraw product outlet takes a portion of the liquid flow that accumulates on the column mass transfer device, preferably a tray, at the side-draw location. Liquid collects in a draw-off box, which is effectively a sump located on the periphery of the side-draw tray, and then exits through a sidedraw nozzle on the side of the column. The balance of liquid that is not thereby withdrawn is used to provide internal reflux to next theoretical separation stage down. The size and location of this sidedraw nozzle in the sidedraw product outlet is carefully set to ensure that the pressure loss as the flow exits the heavy ends column is significantly less than the static head of liquid available in the draw-off box above the sidedraw nozzle. The sidedraw nozzle size and its elevation below the tray from which it is drawn (i.e. the length of the draw-off box) must be set in a specifically calculated manner to avoid two-phase flow.

In this configuration of sidedraw product outlet, the exit pressure loss is calculated from the liquid product exit velocity using a submerged orifice equation. The height from the top of the sidedraw nozzle to the top of the draw-off box is set such that it produces a clear liquid static head which is greater than the equivalent head loss from the submerged orifice equation, a safety factor of 1.5 to 2.5 is also used to account for a degree of froth in the draw-off box. In this way the exit sidedraw nozzle is large enough such that it does not produce a pressure loss that could reduce the liquid below its saturation pressure and cause flashing. The distance from the top of the sidedraw nozzle and the top of the draw-off box is also set to be greater than the diameter of the sidedraw nozzle to avoid the formation of vortexing which may also cause vapour to be drawn into the liquid stream from the tray above; a vortex breaker, typically a "grating type" or "cross-type", may also be used in the draw-off box to achieve the same result in circumstances in which the vertical space is limited. Alternatively, the centreline (rather than the top) of the exit of the sidedraw nozzle as the reference point above which enough liquid height must be available to avoid vortexing or flashing. The use of these measures may effectively ensure that only liquid is always present in the exit sidedraw nozzle, and thus may avoid unstable operation and any production bottlenecks that two-phase flow may cause.

The column mass transfer devices of the heavy end distillation column are not limited, provided that the number of theoretical separation stages and the pressure drop criteria for the middle section of the heavy ends column are fulfilled. Conventional column mass transfer devices used in distillation columns are trays and packing. Trays tend to have a greater pressure drop per theoretical separation stage compared to packing. The use of trays may, however, may be advantageous, especially in the bottom section of the heavy ends column, in that they tend to be constructed from thicker materials than packing and consequently may be able to withstand a higher degree of corrosion before failure.

Provided that the middle section of the heavy ends column comprises the required number of theoretical separation stages and does not exceed the maximum defined pressure drop, the middle section of the heavy ends column may comprise trays, packing or a mixture thereof. In a preferred embodiment of the present invention, the middle section of the heavy ends column comprises packing.

When packing is used in the middle section of the heavy ends column of the present invention, any suitable type of packing that provides the required number of theoretical separation stages without exceeding the maximum allowed pressure drop may be used; examples of suitable types of packing which may be used include, but is not limited to, Pall Rings, Saddles, Raschig Rings, corrugated sheet structured packing, wire-mesh structured packing and grid packings; specific examples of packing which may be used includes Koch Glitsch IMTP (Trade Mark), ULTRA (Trade Mark), FLEXIRING (Trade Mark), HYPAK (Trade Mark), INTALOX saddles (Trade Mark), CMR (Trade Mark), B-ETA ring (Trade Mark), Sulzer I-Rings (Trade Mark), C-Rings (Trade Mark), P-rings (Trade Mark), Nutter Rings (Trade Mark), R-Rings (Trade Mark), Sulzer Mellapak (Trade Mark) (or Mellapak Plus (Trade Mark)), Koch Glitsch Flexipac (Trade Mark) (or Flexipac HC (Trade Mark)), and Koch Glitsch INTALOX (Trade Mark).

The top section of the heavy ends column may comprise trays, packing, or a mixture thereof.

In one embodiment of the present invention, the top section of the heavy ends column comprises packing. Without wishing to be bound by theory, it is believed that the use of packing in the top section of the heavy ends column may provide a slight reduction in the reboiler duty (in terms of energy).

In another embodiment of the present invention, the top section of the heavy ends column comprises trays.

The bottom section of the heavy ends column may comprise trays, packing, or a mixture thereof.

In one embodiment of the present invention, the bottom section of the heavy ends column comprises packing. Without wishing to be bound by theory, it is believed that the use of packing in the bottom section of the heavy ends column may provide a slight reduction in the reboiler duty (in terms of energy) and a slight reduction in reboiler temperature.

In another embodiment of the present invention, the bottom section of the heavy ends column comprises trays.

In one embodiment of the present invention, the stream comprising acetic acid and propionic acid that is fed to the heavy ends column is at least in part in the vapour phase, preferably it is fed to the heavy ends column as a mixed vapour-liquid feed. In a preferred embodiment, the pressure in the heavy ends column at the feed inlet position is below 1.0 bara. The pressure at the feed inlet position at which the stream comprising acetic acid and propionic acid is fed to the heavy ends column is determined by the head pressure of the heavy ends column and the pressure drop between the head of the column and the feed inlet position. A person skilled in the art of distillation would easily be able to determine and control of the pressure at the feed inlet position of the heavy ends column.

The feed inlet of the heavy ends column of the present invention may optionally comprise a feed distribution device; such devices and their use are well known in the art.

The heavy ends column of the present invention is operated under conditions such that the pressure in the heavy ends column above the feed inlet is lower than the pressure of the stream comprising acetic acid and propionic acid that is fed to the heavy ends column.

The heavy ends column of the present invention is operated such that the head pressure is below 1.0 bara. In one particular embodiment of the present invention, the heavy ends column is operated such that the head pressure is below 0.9 bara, preferably below 0.8 bara, more preferably below 0.7 bara. In another particular embodiment of the present invention, the heavy ends column is operated such that the head pressure is in the range of from 0.3 to 0.9 bara, preferably in the range of from 0.4 to 0.8 bara, more preferably in the range of from 0.5 to 0.7 bara.

The control of the head pressure in distillation columns, such as the heavy ends column of the present invention, is well known in the art and any suitable method for vacuum operation of the heavy ends column may be applied.

Due to the heavy ends column of the present invention operating with a head pressure below 1.0 bara, precautions to limit or prevent air ingress in the parts of the column which are below atmospheric pressure may need to be taken, such as the use of welded connections rather than flange-type connections.

In the embodiment wherein the pressure in the heavy ends column at the feed inlet position is below 1.0 bara, the pressure in the middle and top sections of the heavy ends column will be below 1.0 bara, and as such precautions to limit or prevent air ingress in the top and the middle sections of the heavy ends column may need to be taken, such as the use of welded connections rather than flange-type connections. Preferably, all connections in the top and middle section of the column, including the feed inlet, are welded.

In embodiments of the present invention wherein the pressure at the base of the heavy ends column is at or below 1.0 bara, precautions to limit or prevent air ingress in the bottom section of the heavy ends column may need to be taken, such as the use of welded connections rather than flange-type connections. Preferably, all connections in the bottom section of the column are welded.

Advantageously, by use of column mass transfer devices in the bottom section of the heavy ends column of the present invention having a sufficient pressure drop such that the pressure at the base of the column is greater than atmospheric pressure, conventional connections, such as flange-type connections, may be employed in the bottom section of the heavy ends column as the pressure within the bottom section of the heavy ends column would be sufficient to prevent air ingress. For the avoidance of doubt, the bottom section of the heavy ends column does not include the feed inlet but encompasses the part of the heavy ends column below the feed inlet. The use of flange-type connections may provide a more cost effective and simplified construction of the heavy ends column of the present invention compared to the use of welded connections.

Thus, in a preferred embodiment of the present invention, the heavy ends column comprises trays in the bottom section, and has a pressure drop per theoretical separation stage of the bottom section of the heavy ends column of more than 10 mbar, preferably at least 15 mbar per theoretical separation stage of the bottom section of the heavy ends column, even more preferably at least 20 mbar per theoretical separation stage of the bottom section of the heavy ends column.

In another preferred embodiment of the present invention, the heavy ends column comprises trays in the bottom section, and has a pressure drop such that the pressure at the base of the heavy ends column which is greater than atmospheric pressure.

In another preferred embodiment of the present invention, the heavy ends column comprises trays in the bottom section, and has a pressure drop such that the pressure at the base of the heavy ends column is at least 1.05 bara, preferably at least 1.1 bara.

In another preferred embodiment of the present invention, the heavy ends column comprises trays in the bottom section, has a pressure drop per theoretical separation stage of the bottom section of the heavy ends column of more than 10 mbar, preferably at least 15 mbar per theoretical separation stage of the bottom section of the heavy ends column, even more preferably at least 20 mbar per theoretical separation stage of the bottom section of the heavy ends column, and has a pressure drop such that the pressure at the base of the heavy ends column which is greater than atmospheric pressure.

In another preferred embodiment of the present invention, the heavy ends column comprises trays in the bottom section, has a pressure drop per theoretical separation stage of the bottom section of the heavy ends column of more than 10 mbar, preferably at least 15 mbar per theoretical separation stage of the bottom section of the heavy ends column, even more preferably at least 20 mbar per theoretical separation stage of the bottom section of the heavy ends column, and has a pressure drop such that the pressure at the base of the heavy ends column is at least 1.05 bara, preferably at least 1.1 bara.

According to a first aspect of the present invention, there is provided a method of operating a heavy ends column in an acetic acid production unit, said production unit comprising at least a reaction section, a light ends recovery section comprising a light ends distillation column, and a heavy ends column, wherein a stream comprising acetic acid and propionic acid obtained from the light ends recovery section is fed to the heavy ends column through a feed inlet positioned at an intermediate point in the heavy ends column, a product stream comprising essentially acetic acid is withdrawn from the heavy ends column through a sidedraw product outlet position above the feed inlet, and a product stream comprising the propionic acid is withdrawn from the heavy ends column through a heavy product outlet positioned below the feed inlet, wherein the heavy ends column is operated under conditions such that the pressure in the heavy ends column above the feed inlet is lower than the pressure of the stream comprising acetic acid and propionic acid that is fed to the heavy ends column, and wherein the head pressure of the heavy ends column is below 1.0 bara, the number of theoretical separation stages between the feed inlet and the sidedraw product outlet is at least 5, preferably at least 7, more preferably at least 10, and the pressure drop in the part of the heavy ends column between the feed inlet and the sidedraw product outlet is at most 10 mbar per theoretical separation stage.

According to a further aspect of the present invention, there is provided a process for the separation of acetic acid from a stream comprising acetic acid and propionic acid, wherein said stream is fed to a distillation column having features corresponding to the heavy ends column as defined above, and operated in accordance with the operation of the heavy ends column as defined above.

According to a further aspect of the present invention, there is provided a process for the production of acetic acid in an acetic acid production unit comprising a reaction section, a light ends recovery section comprising a light ends column, and a heavy ends column, wherein said process comprises the steps:

(a) in the reaction section, carbonylating methanol and/or a reactive derivative thereof with carbon monoxide in a liquid reaction composition comprising a Group VIII metal carbonylation catalyst, a methyl iodide cocatalyst, acetic acid, water, methyl acetate, propionic by-product, and optionally a promoter;

(b) withdrawing at least a portion of the liquid reaction composition from the reaction section and introducing the withdrawn liquid reaction composition into a flash zone to produce a vapour fraction comprising water, acetic acid, methyl acetate, methyl iodide, and propionic acid by-product, and a liquid fraction comprising the catalyst;

(c) recycling the liquid fraction from the flash zone to the reaction section;

(d) feeding the vapour fraction obtained from the flash zone to the light ends column of the light ends recovery section;

(e) removing a stream comprising acetic acid and propionic acid from the light ends column;

(f) optionally drying the stream comprising acetic acid and propionic acid removed from the light ends column in a separate drying column; and (g) feeding the stream comprising acetic acid and propionic acid to the heavy ends column through a feed inlet positioned at an intermediate point in the heavy ends column, withdrawing a product stream comprising essentially acetic acid through a sidedraw product outlet position above the feed inlet, and withdrawing a product stream comprising the propionic acid through a heavy product outlet positioned below the feed inlet, wherein the heavy ends column is a heavy ends column having features corresponding to the heavy ends column as defined above, and operated in accordance with the operation of the heavy ends column as defined above.

EXAMPLE

The operation of heavy end columns according to the present invention and heavy end columns falling outside of the present invention were simulated using an ASPEN PLUS (Trademark) (version 7.3) computer model. The heavy ends column in the simulation comprised a feed inlet positioned at an intermediate point in the heavy ends column, a sidedraw product outlet position above the feed inlet, and a heavy product outlet positioned below the feed inlet, and was separated in to three sections: a top section defined as the part of the column above the sidedraw product outlet; a middle section defined as the part of the column between the sidedraw product outlet and the feed inlet; and, a bottom section defined as the part of the column below the feed inlet. For each section of the column, two different types of column internals, trays and packing, were simulated. The details of the parameters used in each of the three sections of the heavy end column simulated are provided in Table 1.

TABLE 1

| Column Section | Number of theoretical separation stages | Pressure Drop (mBar) | |
|---|---|---|---|
| | | Tray | Packing |
| Top | 3 | 40 | 6 |
| Middle | 12 | 270 | 25 |
| Bottom | 18 | 500 | 55 |

The simulated operation of the heavy ends column was performed using a fixed feed inlet composition and a fixed sidedraw product outlet composition as defined in Table 2 below.

TABLE 2

| | % w/w Inlet | % w/w Product |
|---|---|---|
| Methanol | 0.003 | 0.002 |
| Methyl Acetate | 0.002 | 0.001 |
| Acetic Acid | 99.795 | 99.863 |
| Water | 0.100 | 0.104 |
| Propionic Acid | 0.100 | 0.030 |
| Total | 100.000 | 100.000 |

The operation of all eight possible permutations of the heavy ends column was simulated using a fixed inlet temperature of 156° C., a fixed inlet pressure of 6 Bara, a fixed head pressure of 0.565 Bara, and a sub cooled temperature set point of 70° C. in the condenser. The results of the simulation are provided in Table 3 below.

TABLE 3

| Column Internals (Top/Middle/Bottom)* | Reboiler Duty (MW/tn of product) | Condenser Duty (MW/tn of product) | Molar Reflux Ratio | Feed Pressure (bara) | Base Pressure (bara) | Base Temperature (° C.) |
|---|---|---|---|---|---|---|
| T/T/T | 0.185 | 0.231 | 33.39 | 0.875 | 1.375 | 129.3 |
| T/T/P | 0.183 | 0.229 | 33.11 | 0.875 | 0.93 | 116.3 |
| P/T/T | 0.183 | 0.230 | 33.26 | 0.841 | 1.341 | 128.5 |
| P/T/P | 0.181 | 0.228 | 32.98 | 0.841 | 0.896 | 115.1 |
| T/P/T | 0.172 | 0.217 | 31.42 | 0.63 | 1.13 | 122.7 |
| T/P/P | 0.170 | 0.216 | 31.14 | 0.63 | 0.685 | 106.7 |
| P/P/T | 0.170 | 0.216 | 31.24 | 0.596 | 1.096 | 121.6 |
| P/P/P | 0.168 | 0.214 | 30.95 | 0.596 | 0.651 | 105.1 |

*T = Tray; P = Packing

BRIEF DESCRIPTION OF THE DRAWINGS

The invention is further described with reference to the accompanying drawings, in which.

Figure 1:
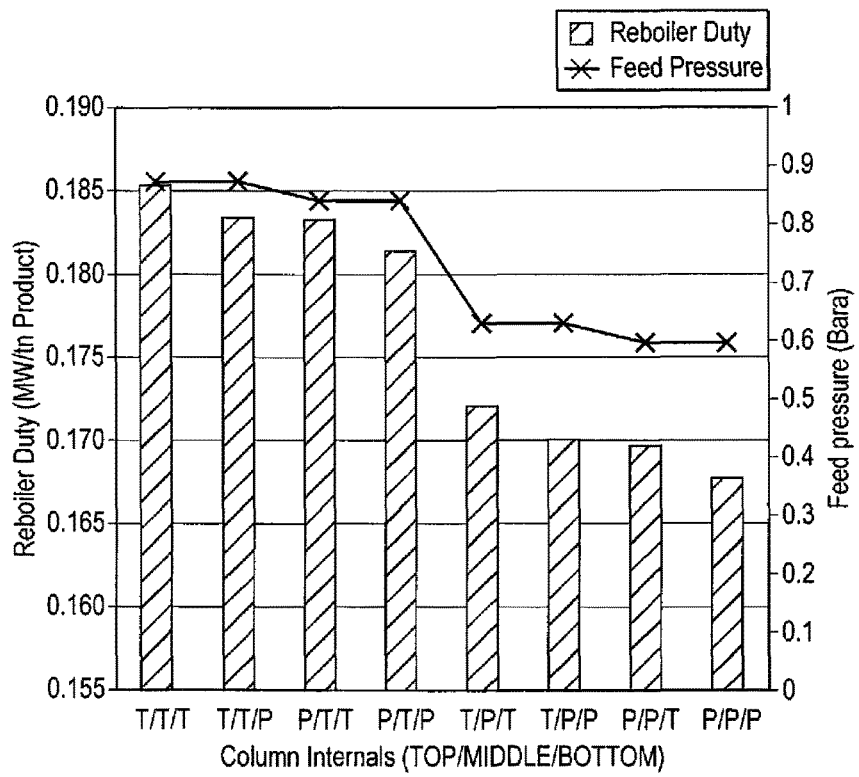
FIG. 1 plots the reboiler duty in terms MW per ton of acetic acid product and also plots the feed pressure for all of the permutations of the heavy ends column simulated.
Figure 2:
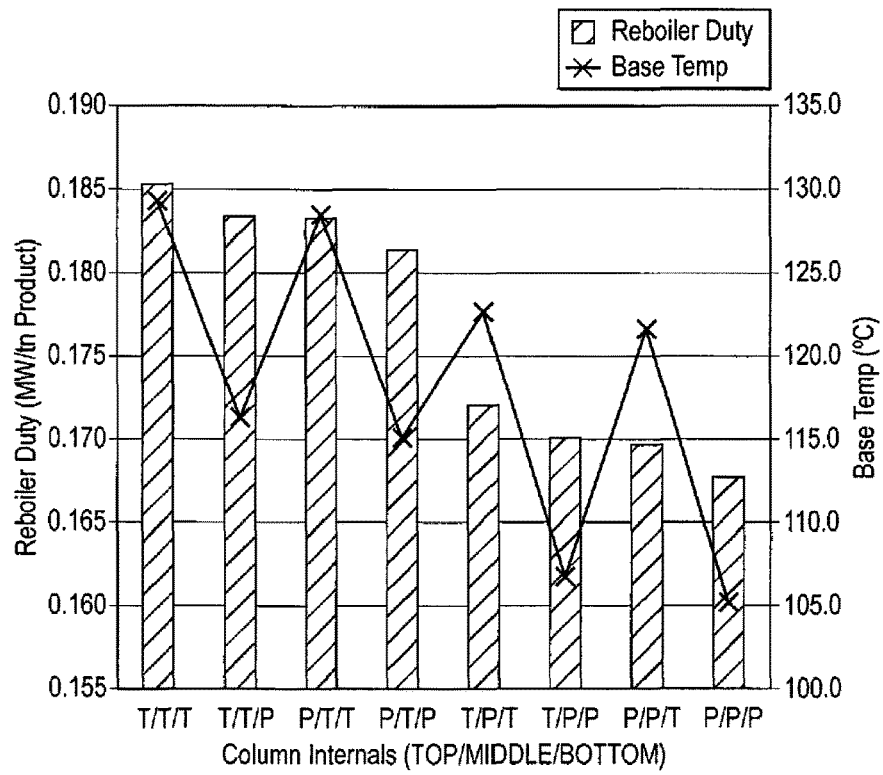
FIG. 2 plots the reboiler duty in terms MW per ton of acetic acid product and also plots the column base temperature for all of the permutations of the heavy ends column simulated.

As can be clearly seen from the results, the reboiler duty required when the middle section of the heavy ends column comprises packing is significantly reduced compared to when the middle section of the heavy ends column comprises trays. The feed pressure also followed the general trend seen in reboiler duty across all permutations (i.e. as feed pressure is lowered, the reboiler duty decreases).

When packing was used in the bottom section, the largest reduction in column base temperature was observed, however, the use of packing in the bottom section had a significantly less significant effect on reducing reboiler duty than the use of a lower feed pressure as occurs in the heavy end columns comprising packing in the middle section.

The invention claimed is:

1. A method of operating a heavy ends column in an acetic acid production unit, said production unit comprising at least a reaction section, a light ends recovery section comprising a light ends distillation column, and a heavy ends column, wherein a stream comprising acetic acid and propionic acid obtained from the light ends recovery section is fed to the heavy ends column through a feed inlet positioned at an intermediate point in the heavy ends column, a product stream comprising essentially acetic acid is withdrawn from the heavy ends column through a sidedraw product outlet position above the feed inlet, and a product stream comprising the propionic acid is withdrawn from the heavy ends column through a heavy product outlet positioned below the feed inlet, wherein the heavy ends column is operated under conditions such that the pressure in the heavy ends column above the feed inlet is lower than the pressure of the stream comprising acetic acid and propionic acid that is fed to the heavy ends column, and wherein the head pressure of the heavy ends column is below 1.0 bara, the number of theoretical separation stages between the feed inlet and the sidedraw product outlet is at least 5, and the pressure drop in the part of the heavy ends column between the feed inlet and the sidedraw product outlet is at most 10 mbar per theoretical separation stage.

2. A method according to claim 1, wherein the pressure in the heavy ends column at the feed inlet position is below 1.0 bara.

3. A method according to claim 1, wherein the heavy ends column comprises packing in the part of the heavy ends column between the feed inlet and the sidedraw product outlet.

4. A method according to claim 1, wherein the heavy ends column comprises trays in the part of the heavy ends column below the feed inlet.

5. A method according to claim 1, wherein the heavy ends column comprises trays in the part of the heavy ends column above the sidedraw product outlet.

6. A method according to claim 1, wherein the head pressure of the heavy ends column is below 0.9 bara.

7. A method according to claim 1, wherein the head pressure of the heavy ends column is in the range of from 0.3 to 0.9 bara.

8. A method according to claim 1, wherein the number of theoretical stages between the feed inlet and the sidedraw product outlet is in the range of from 10 to 20.

9. A method according to claim 1, wherein the pressure drop in the part of the heavy ends column between the feed inlet and the sidedraw product outlet is at most 80 mbar.

10. A method according to claim 1, wherein the heavy ends column comprises trays in the part of the heavy ends column below the feed inlet, and has a pressure drop such that the pressure at the base of the heavy ends column is greater than atmospheric pressure.

11. A method according to claim 1, wherein the light ends recovery section of the acetic acid production unit comprises a light ends distillation column and a drying column.

12. A method according to claim 1, wherein the light ends recovery section of the acetic acid production unit comprises a combined light ends distillation and drying column.

13. A method according to claim 1, wherein the acetic acid production unit comprises a flash zone between the reactor and the light ends recovery section.

14. A process for the separation of acetic acid from a stream comprising acetic acid and propionic acid, wherein in said process the stream comprising acetic acid and propionic acid is fed to a distillation column through a feed inlet positioned at an intermediate point in the distillation column, a product stream comprising essentially acetic acid is withdrawn from the distillation column through a sidedraw product outlet position above the feed inlet, and a product stream comprising the propionic acid is withdrawn from the distillation column through a heavy product outlet positioned below the feed inlet, wherein the distillation column is operated under conditions such that the pressure in the distillation column above the feed inlet is lower than the pressure of the stream comprising acetic acid and propionic acid that is fed to the distillation column, and wherein the distillation column configured such that the head pressure is below 1.0 bara, the number of theoretical separation stages between the feed inlet and the sidedraw product outlet is at least 5, and the pressure drop in the part of the distillation column between the feed inlet and the sidedraw product outlet is at most 10 mbar per theoretical separation stage.

15. A process for the production of acetic acid in an acetic acid production unit comprising a reaction section, a light ends recovery section comprising a light ends column, and a heavy ends column, wherein said process comprises the steps:
   (a) in the reaction section, carbonylating methanol and/or a reactive derivative thereof with carbon monoxide in a liquid reaction composition comprising a Group VIII metal carbonylation catalyst, a methyl iodide cocatalyst, acetic acid, water, methyl acetate and propionic by-product;
   (b) withdrawing at least a portion of the liquid reaction composition from the reaction section and introducing the withdrawn liquid reaction composition into a flash zone to produce a vapour fraction comprising water, acetic acid, methyl acetate, methyl iodide, and propionic acid by-product, and a liquid fraction comprising the catalyst;
   (c) recycling the liquid fraction from the flash zone to the reaction section;
   (d) feeding the vapour fraction obtained from the flash zone to the light ends column of the light ends recovery section;
   (e) removing a stream comprising acetic acid and propionic acid from the light ends column;
   and
   (f) feeding the stream comprising acetic acid and propionic acid to the heavy ends column through a feed inlet positioned at an intermediate point in the heavy ends column, withdrawing a product stream comprising essentially acetic acid through a sidedraw product outlet position above the feed inlet, and withdrawing a product stream comprising the propionic acid through a heavy product outlet positioned below the feed inlet,
   wherein the heavy ends column is operated under conditions such that the pressure in the heavy ends column above the feed inlet is lower than the pressure of the stream comprising acetic acid and propionic acid that is fed to the heavy ends column, and wherein the head pressure of the heavy ends column is below 1.0 bara, the number of theoretical separation stages between the feed inlet and the sidedraw product outlet is at least 5, and the pressure drop in the part of the heavy ends column between the feed inlet and the sidedraw product outlet is at most 10 mbar per theoretical separation stage.

16. A method according to claim 1, wherein the number of theoretical separation stages between the feed inlet and the sidedraw product outlet is at least 7.

17. A method according to claim 1, wherein the number of theoretical separation stages between the feed inlet and the sidedraw product outlet is at least 10.

18. A method according to claim 6, wherein the head pressure of the heavy ends column is below 0.8 bara.

19. A method according to claim 6, wherein the head pressure of the heavy ends column is below 0.7 bara.

20. A method according to claim 7, wherein the head pressure of the heavy ends column is in the range of from 0.4 to 0.8 bara.

21. A method according to claim 7, wherein the head pressure of the heavy ends column is in the range of from 0.5 to 0.7 bara.

22. A method according to claim 8, wherein the number of theoretical stages between the feed inlet and the sidedraw product outlet is in the range of from 12 to 16.

23. A method according to claim 9, wherein the pressure drop in the part of the heavy ends column between the feed inlet and the sidedraw product outlet is at most 60 mbar.

24. A process according to claim 14, wherein the number of theoretical separation stages between the feed inlet and the sidedraw product outlet is at least 7.

25. A process according to claim 14, wherein the number of theoretical separation stages between the feed inlet and the sidedraw product outlet is at least 10.

26. A process according to claim 15, wherein the liquid reaction composition in step (a) comprises a promoter.

27. A process according to claim 15, further comprising drying the stream comprising acetic acid and propionic acid removed from the light ends column in a separate drying column.

28. A process according to claim 15, wherein the number of theoretical separation stages between the feed inlet and the sidedraw product outlet is at least 7.

29. A process according to claim 15, wherein the number of theoretical separation stages between the feed inlet and the sidedraw product outlet is at least 10.

* * * * *